(12) United States Patent
Parsons et al.

(10) Patent No.: US 7,842,689 B2
(45) Date of Patent: Nov. 30, 2010

(54) CYCLIC HYDROXYLAMINE AS PSYCHOACTIVE COMPOUNDS

(75) Inventors: Phillip Parsons, Brighton (GB); Silvia Trasciatti, Pisano (IT); Sergio Rosini, Pisano (IT); Michael Annis, Hove (GB)

(73) Assignee: BTG International Limited, London (GB)

( * ) Notice: Subject to any disclaimer, the term of this patent is extended or adjusted under 35 U.S.C. 154(b) by 1175 days.

(21) Appl. No.: 10/559,180

(22) PCT Filed: Jun. 1, 2004

(86) PCT No.: PCT/GB2004/002324

§ 371 (c)(1),
(2), (4) Date: Feb. 2, 2006

(87) PCT Pub. No.: WO2004/111021

PCT Pub. Date: Dec. 23, 2004

(65) Prior Publication Data

US 2006/0142286 A1 Jun. 29, 2006

(30) Foreign Application Priority Data

Jun. 12, 2003 (GB) ................................. 0313628.0
Dec. 8, 2003 (GB) ................................. 0328439.5

(51) Int. Cl.
*A61K 31/535* (2006.01)
*C07D 265/22* (2006.01)
*C07D 265/32* (2006.01)

(52) U.S. Cl. .................................... 514/231.2; 544/173
(58) Field of Classification Search ................. 544/173; 514/231.2

See application file for complete search history.

(56) References Cited

U.S. PATENT DOCUMENTS 5,476,867 A 12/1995 Boyd et al.
5,707,988 A 1/1998 Boyd et al.

FOREIGN PATENT DOCUMENTS

JP 05-255250 A 10/1993
WO WO 90/14342 A1 11/1990
WO WO 95/17385 A1 6/1995

OTHER PUBLICATIONS

Science (1999), vol. 286, 531-537.*
Cancer and Metastasis Reviews (1998), 17(1), 91-106.*
Murahashi et al., Tetrahedron Letters, vol. 26, No. 38, pp. 4633-4636, 1985.*
Ali, S.A., et al; "Mercury(II) oxide Oxidation of 2-Substituted-N-hydroxypiperidine: A Solution to the Regiochemical Problem"; *Tetrahedron Letters*, vol. 34, No. 33, pp. 5325-5326 (1993).
Ali, S.A., et al; "Regiochemistry of Mercury(II) oxide Oxidation of Unsymmetrical N,N-Disubstituted Hydroxylamines"; *Tetrahedron*, vol. 52, No. 47, pp. 14917-14928 (1996).
Ali, S.A., et al; "Synthesis and Cycloaddition of 6-Substituted 3,4,5,6-Tetrahydropyridine 1-Oxides"; *J. Chem. Research*; Synop., vol. 2, pp. 54-55 (1994).
Banerji, A., et al; "Cycloaddition of C,N-Diarylnitrones to 2-Butenolide: Synthesis of 2,3,6,6a-Tetrahydrofuro[3,4-d]isoxazol-4(3aH)-one"; *Tetrahedron*, vol. 48, No. 16, pp. 3335-3344 (1992) XP-001026252.

(Continued)

*Primary Examiner*—Rebecca L Anderson
(74) *Attorney, Agent, or Firm*—Nixon & Vanderhye

(57) ABSTRACT

A compound of formula (II):

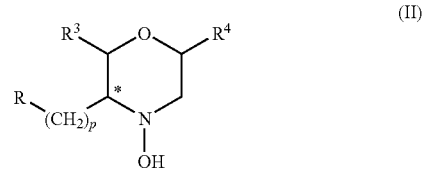

in which—
$R^3$ and $R^4$ each independently represent hydrogen or $C_{1-6}$ alkyl; p represent 0 or 1; and
R represents a five- or six-membered saturated or unsaturated ring selected from:

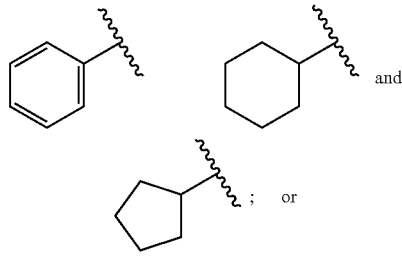

R represents a five- or six-membered substituted or unsubstituted unsaturated ring selected from:

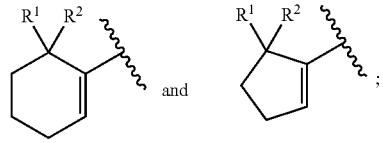

wherein $R^1$ and $R^2$ together represent an oxo group, or $R^1$ and $R^2$ each represent hydrogen, methoxy or ethoxy, or $R^1$ and $R^2$ together with the interjacent carbon atom represent a 1,3-dioxolane or 1,3-dioxane ring, attached via the 2 position and optionally bearing one or more methyl or ethyl groups; or a salt thereof, which is suitable for the treatment of anxiety and depression.

10 Claims, No Drawings

OTHER PUBLICATIONS

DeMarch, P., et al; "Asymmetric Induction in the Cycloaddition of a Masked *p*-Benzoquinone to Cyclic Nitrones"; *J. Org. Chem.*; vol. 62, pp. 7781-7787 (1997) XP-002296430.

DeMarch, P., et al; "Efficient Masking of *p*-Benzoquinone in Nitrone Cycloaddition Chemistry"; *Tetrahedron Letters*; vol. 36, No. 47, pp. 8665-8668 (1995).

Elsworth, J.F., et al; "Nitrones. Part IX. The Synthesis and Reactions of 2,3-Dihydro-1,4-oxazine 4-Oxide, a Heterocyclic Nitrone"; *Journal of the Chemical Society*; Section C: Organic Chemistry, No. 19, pp. 2423-2427 (1968) XP-001027088.

Kato, T., et al; "Reaction of Pyridine and Quinoline N-Oxides with Phenylmagnesium Bromide"; *Y. Org. Chem.*; vol. 30, No. 3, pp. 910-913 (1965).

Thesing, J., et al; "Cyclische Nitrone I: Dimeres 2,3,4,5-Tetrahydro-pyridin-*N*-oxyd"; *Chem. Ber.*, vol. 89, pp. 2159-2167 (1956).

* cited by examiner

CYCLIC HYDROXYLAMINE AS PSYCHOACTIVE COMPOUNDS

This application is the U.S. National Phase of International Application PCT/GB2004/002324, filed 1 Jun. 2004, which designated the U.S. PCT/GB2004/002324 claims priority to British Application No. 0313628.0, filed 12 Jun. 2003 and British Application No. 0328439.5, filed 8 Dec. 2003. The entire content of these applications are incorporated herein by reference.

This invention relates to psychoactive compounds suitable for the treatment of anxiety and depression. In particular, this invention relates to novel hydroxylamine compounds such as ring-opened derivatives of isoxazole compounds and their analogues, their preparation, pharmaceutical formulations thereof and their use in medicine.

A number of psychoactive compounds are known for use in the treatment of anxiety and depression. Diazepam (a benzodiazepine) is well-known, and widely used as an anxiolytic and anti-depressant. Other known psychoactive compounds include certain tricyclic fused benzo[d]isoxazole compounds having the structure shown below in formula (A), as disclosed in U.S. Pat. No. 5,707,988 (Boyd et al./British Technology Group Ltd.):

(A)

in which X' is O, S, C=O or NR' wherein R' is hydrogen, $C_{1-6}$ alkyl, phenyl or $C_{7-12}$ phenalkyl, $R_1'$ and $R_2'$ each represent hydrogen or together represent an oxo group and $R_3'$, $R_4'$ and $R_5'$ each represent hydrogen or $R_1'$ represents hydrogen and two of $R_2'$, $R_3'$, $R_4'$ and $R_5'$ together represent the second bond of a double bond joining positions 7 and 8, 8 and 9 or 9 and 10 with the remaining two of $R_2'$, $R_3'$, $R_4'$ and $R_5'$ representing hydrogen, or a salt thereof.

It has been found that, although the compounds of formula (A) demonstrate good efficacy as anxiolytic agents, their efficacy in the treatment of depression is less than ideal. There is therefore a need for new compounds that are effective in the treatment of both anxiety and depression, in particular for the treatment of pathologies in which both conditions occur. The present invention addresses that need.

The following compounds are known as synthetic intermediates:

[P5]

2-phenylpiperidin-1-ol

[P6]

2-benzylpiperidin-1-ol

2-Phenylpiperidin-1-ol is mentioned in the following papers:

"Regiochemistry of mercury(II) oxide oxidation of unsymmetrical N,N-disubstituted hydroxylamines." *Tetrahedron* (1996), 52(47), 14917-28 (Ali et al.);

"Reaction of pyridine and quinoline N-oxides with phenylmagnesium bromide." *Y. Org. Chem.* (1965), 30(3), 910-13 (Kato et al.);

"Cyclic nitrones (I): dimeric 2,3,4,5-tetrahydropyridine N-oxides." *Chem. Ber.*, vol. 89, 2159-67 (1956) (Thesing et al.).

2-Benzylpiperidin-1-ol is mentioned in the following papers:

"Synthesis and cycloaddition of 6-substituted 3,4,5,6-tetrahydropyridine 1-oxides." *J. Chem. Res.*, Synop. (1994), (2), 54-5 (Ali et al.);

"Mercury(II) oxide oxidation of 2-substituted N-hydroxypiperidine: a solution to the regiochemical problem." *Tet. Lett.* (1993), 34(33), 5325-6 (Ali et al.).

However, there is no disclosure of the compounds for use as pharmaceuticals.

Accordingly, the present invention provides in a first aspect a compound of formula (I):

(I)

in which—

X represents O or $CH_2$;

$R^3$ and $R^4$ each independently represent hydrogen or $C_{1-6}$ alkyl;

p represent 0 or 1; and

R represents a five- or six-membered saturated or unsaturated ring selected from:

and  ; or

R represents a five- or six-membered exe-substituted or unsubstituted unsaturated ring selected from:

wherein $R^1$ and $R^2$ together represent an oxo group, or $R^1$ and $R^2$ each represent hydrogen, methoxy or ethoxy, or $R^1$ and $R^2$ together with the interjacent carbon atom represent a 1,3-dioxolane or 1,3-dioxane ring, attached via the 2 position and optionally bearing one or more methyl or ethyl groups;

or a tautomer thereof;

or a salt thereof;

for use as a pharmaceutical.

In the case where R represents a five- or six-membered axe-substituted or unsubstituted unsaturated ring selected from:

wherein $R^1$ and $R^2$ together represent an oxo group, or an acetal thereof, wherein $R^1$ and $R^2$ each represent methoxy or ethoxy, or $R^1$ and $R^2$ together with the interjacent carbon atom represent a 1,3-dioxolane or 1,3-dioxane ring, attached via the 2 position and optionally bearing one or more methyl or ethyl groups, then preferably p represents 0. The invention thus preferably embraces compounds of formula (IA), (IB), (IC) (ID), (IE) and (IF):

(IA)
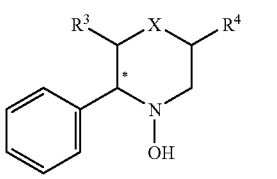

(IB)
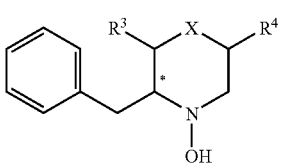

(IC)
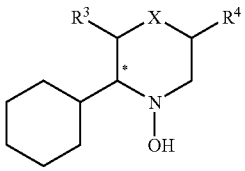

(ID)
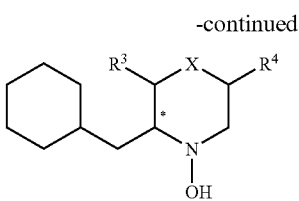

(IE)
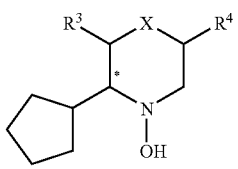

(IF)
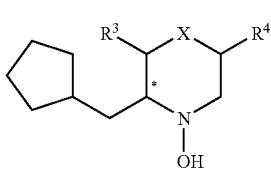

as well as ketones of formula (IG) and (IH):

(IE)
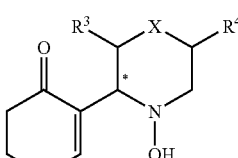

(IF)
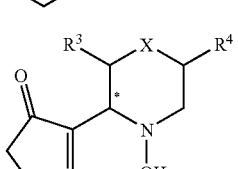

and acetals of the ketones of formula (IG) or (IH) with methanol or ethanol; or with ethane-1,2-diol or propane-1,2-diol, optionally bearing one or more methyl or ethyl groups.

When $R^1$ and $R^2$ together with the interjacent carbon atom represent a 1,3-dioxolane or 1,3-dioxane ring bearing one or more methyl or ethyl groups, preferably one methyl or ethyl group is positioned adjacent to each of the oxygen atoms in the 1,3-dioxolane or 1,3-dioxane ring. Preferably these are in the trans orientation, giving a compound such as:

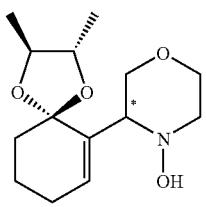

Such compounds might be hydrolysed in vivo to produce the corresponding compound of formula (I) in which $R^1$ and $R^2$ together represent an oxo group. The compounds having the 3-dioxolane or 1,3-dioxane ring therefore represent potential prodrugs.

However, preferably $R^1$ and $R^2$ together represent an oxo group.

In the case where R represents a five- or six-membered substituted or unsubstituted unsaturated ring selected from:

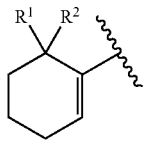 and 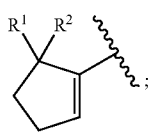;

then preferably X is O.

Synthesis is facilitated if the heterocyclic ring demonstrates some symmetry Thus preferably $R^3$ and $R^4$ are identical. Preferably $R^3$ and $R^4$ each represents hydrogen.

In a second aspect, the present invention provides a compound of formula (II):

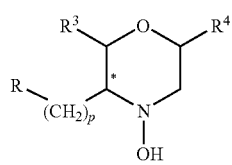

(II)

in which—

$R^3$ and $R^4$ each independently represent hydrogen or $C_{1-6}$ alkyl;

p represent 0 or 1; and

R represents a five- or six-membered saturated or unsaturated ring selected from:

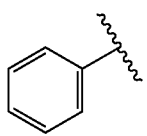 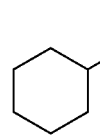 and 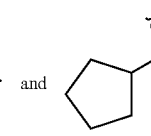; or

R represents a five- or six-membered substituted or unsubstituted unsaturated ring selected from:

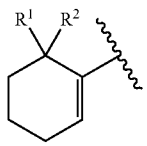 and 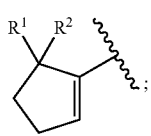;

wherein $R^1$ and $R^2$ together represent an oxo group, or $R^1$ and $R^2$ each represent hydrogen, methoxy or ethoxy, or $R^1$ and $R^2$ together with the interjacent carbon atom represent a 1,3-dioxolane or 1,3-dioxane ring, attached via the 2 position and optionally bearing one or more methyl or ethyl groups;

or a tautomer thereof;

or a salt thereof.

A further preferred embodiment of the present invention is a compound of formula (III):

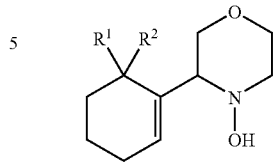

(III)

in which—

$R^1$ and $R^2$ each represent hydrogen or together represent an oxo group; or a salt thereof.

In this specification the term "alkyl" includes both straight and branched chain groups, as well as saturated and unsaturated groups.

When $R^1$ and $R^2$ together represent an oxo group, certain compounds of the invention might exist as tautomers where the N-hydroxyl group has reacted with the carbonyl group to form a hemiacetal of formula (IV) or (V):

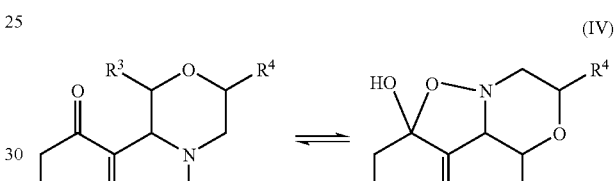

(IV)

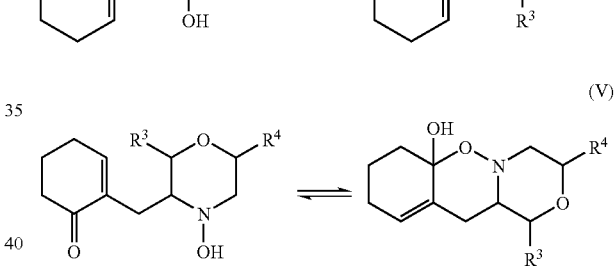

(V)

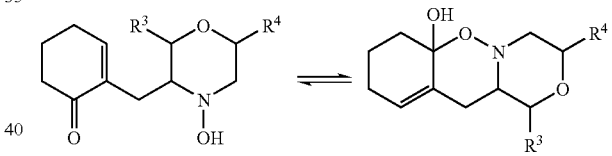

Thus the hemiacetals of formula (IV) and (V) are within the scope of the invention.

As indicated above, the compounds of the invention may exist in the form of a salt, preferably an amine salt. Such salts may be formed with a physiologically acceptable inorganic or organic acid. Physiologically acceptable acids include hydrochloric, hydrobromic, sulfuric, nitric, phosphoric, isethionic, acetic, fumaric, maleic, salicylic, p-toluenesulfonic, tartaric, citric, lactobionic, formic, malonic, pantothenic, succinic, naphthalene-2-sulfonic, benzenesulfonic, methanesulfonic and ethanesulfonic acid. Hydrochloric acid is preferred. However, in general it is preferred to use the free base rather than the salt.

The compounds of the invention possess a chiral centre (denoted *) at the carbon atom adjacent the nitrogen of the N—OH group. It will be appreciated that the compounds of the invention can be resolved into their enantiomeric forms, or exist as a racemate. Depending on the nature of the substituents, a number of diastereoisomers is also possible.

In the case where p represents 0 and R represents a five- or six-membered substituted or unsubstituted unsaturated ring selected from:

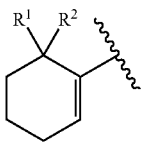 and 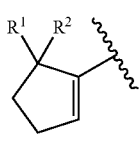

the compounds of the invention may be prepared by the reaction of a compound of formula (VI) or (VIA) with a compound of formula (VII):

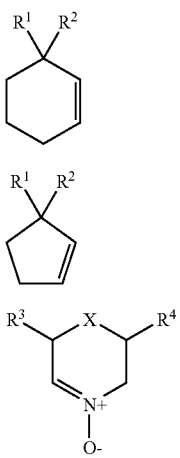

(VI)

(VIA)

(VII)

in which $R^1$, $R^2$ and X are as defined with respect to formula (I). It will be appreciated that this will be most straightforward when $R^1$ and $R^2$ together represent an oxo group, as the double bond compound of formula (VI) or (VIA) will then be activated by the presence of the carbonyl group. Other electron-withdrawing groups would also facilitate reaction.

The reaction is preferably carried out by combining the compounds of formulae (VI) or (VIA) and (VII) at a temperature in the range of from room temperature to 100° C., and then heating the reaction mixture to a temperature in the range of from 50 to 150° C., more preferably 55 to 65° C. for several hours in a suitable solvent. Ambient pressure may be used, but preferably the reaction is carried out at ultrahigh pressure in a sealed tube. The compound of formula (VI) or (VIA) may itself be a suitable solvent for the reaction; for example, in the case where $R^1$ and $R^2$ together represent an oxo group, the resultant 2-cyclohexenone and 2-cyclopentenone are both readily available.

The compound of formula (I) is thereby produced via the formation of a tricyclic intermediate of formula (VII) or (VIIIA):

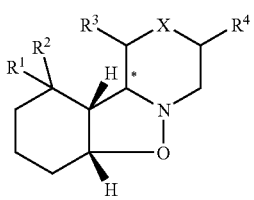

(VIII)

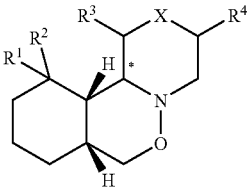

(VIIIA)

which may be isolated or left to remain in situ. Protonation of the intermediate (VIII) or (VIIIA), or a corresponding base-catalysed reaction, leads to the formation of compound (I). Ring opening presumably appears by an E1cb elimination ("cb" denoting "conjugate base"), or the corresponding acid-catalysed reaction, preferably at elevated temperature.

The compound of formula (VII) is preferably formed in situ from a compound of formula (IX):

(IX)

via oxidation, preferably a pertungstate-catalysed oxidation. The nitrone (VII) has a tendency to polymerise and, if it needs to be isolated, care should be taken to avoid polymerise happening by storing in a freezer.

Any of the compounds of the invention may also be prepared by the reaction of a Grignard reagent of formula $R(CH_2)_p MgHal$ with a compound of formula (VII):

(VII)

in which Hal represents halide and R, $R^1$, $R^2$ and X are as defined with respect to formula (I). We have fund that the Grignard reagents prepared using a chloride anion to be perfectly satisfactory.

The reaction is preferably carried out by combining the Grignard reagent of formula $R(CH_2)_p MgHal$ with the compound of formula (VII) at a temperature of $-10°$ C., and then holding the reaction mixture at a temperature of 0° C. in a suitable solvent. Tetrahydrofuran is a suitable solvent for the reaction.

It will be appreciated that the compounds of formula (I) may also be prepared by modifications of these processes and by other alternative processes, which will be apparent to a person skilled in the chemical art.

The compounds of the invention have been found to effective in the treatment of both anxiety and depression. They are particularly useful for the treatment of anxiogenesis caused by withdrawal from benzodiazepines (as they exhibit cross tolerance with these benzodiazepines in comparison with buspirone, for example, which does not). The compounds are also of use in the treatment of anxiogenesis caused by abruptly ceasing the administration of drugs of abuse such as nicotine, alcohol and cocaine.

The dosage level of the compounds of formula (I) required to achieve effective anxiolysis or anti-depressant activity will vary with the mammal treated and will depend on factors such as the mammal's body weight, its surface area, age and general state of health. It will also depend upon the mode of administration. Dosage levels of 0.01 mg/kg to 100 mg/kg, particularly 1 mg/kg to 10 mg/kg, are suitable. Depending upon the nature and severity of the condition being treated, the doses may be repeated up to 2 or 3 times per day during the period of treatment. Doses outside these ranges may be administered if appropriate.

The compounds of formula (I) may be administered using oral, rectal, parenteral, subcutaneous or topical routes.

The compounds of formula (I) may be administered alone or together with a pharmaceutically acceptable carrier, such as an excipient or diluent. The invention therefore further provides a pharmaceutical composition comprising a compound of formula (I) in association with a pharmaceutically acceptable carrier therefor. The composition may further comprise additional therapeutic agent(s) or ingredient(s).

The compounds and compositions of the invention may conveniently be presented as unit dosage forms prepared using techniques that are well known to a person skilled in the art. In general, preparation of the unit dosage form includes the step of bringing one or more therapeutically active compounds into association with the carrier. The active compound(s) or and/or carrier ingredient(s) are preferably in the form of a finely divided solid or a liquid.

Compositions suitable for oral administration include discreet units such as tablets, capsules, caplets, cachets or lozenges, each containing a predetermined amount of the therapeutic compound. Solutions and suspensions of the therapeutic compound in an aqueous or a non-aqueous liquid are also suitable for oral administration and include syrups, elixirs and emulsions. The compound may also be presented as a bolus, electuary or paste.

Administration of the compound by a parenteral routes includes intravenous, intraperitoneal, intra-muscular and intra-articular administration. Compositions suitable for parenteral administration conveniently include a sterile aqueous preparation of the active compound, suitable for injection or infusion Compositions suitable for topical administration include lotions, creams and pastes. The compositions of the invention may also be presented in the form of an aerosol or a suppository.

Accordingly the present invention also provides a method for preventing or alleviating the symptoms of anxiety and/or depression, which method comprises administering to a patient in need of such treatment, particularly a warm-blooded animal such as a human, a non-toxic, therapeutically effective amount of a compound of a compound of formula (I), or a salt thereof, or a composition containing such a compound.

The invention also includes a compound of formula (I) for use as a medicament, and the use of a compound of formula (I), or a salt thereof, in the manufacture of a medicament for treatment of both anxiety and depression, particularly for the treatment of anxiogenesis caused by withdrawal from benzodiazepines, or caused by abruptly ceasing the administration of drugs of abuse such as nicotine, alcohol and cocaine.

The invention will now be described by reference to the following Examples. Variations on these Examples falling within the scope of the invention will be apparent to a person skilled in the art.

EXAMPLES

Example 1

Preparation of 2-(4-hydroxy-3-morpholinyl)-2-cyclohexenone

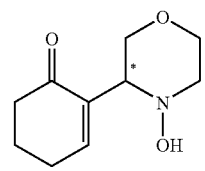

Morpholine (10.97 g; 0.126 M) and sodium tungstate hydrate (1.54 g; 4.67 mM) were cooled to 0° C. in a 250 mL flask. Hydrogen peroxide (32.5 mL (30% aq.); 0.286 mM) was slowly added, keeping the reaction temperature at 0° C. The reaction mixture was stirred for a further 1.5 h and excess hydrogen peroxide was destroyed using sodium bisulfate. 2-Cyclohexenone (12.1 mL; 0.12 5M) was added slowly to the flask, and the reaction mixture was stirred for a further 48 h. The reaction mixture was heated to 55° C. for 2 h and then 65° C. for a further 2 h. The reaction mixture was then poured into aqueous sodium chloride and was extracted with dichloromethane (3×100 mL). The organic layer was washed with saturated sodium bicarbonate solution, separated and dried over magnesium sulfate. Removal of the solvent gave a light brown oil, which was subjected to Kugelrohr distillation at 50-60° C. under vacuum, producing a dark oil (3.5 g; 14%). The compound was further purified by chromatography on a silica column using a dichloromethane ($CH_2Cl_2$): acetonitrile ($CH_3CN$) eluent (5:1; 0.27).

$v_{max}$ ($cm^{-1}$)=3435 (OH); 2958, 2941, 2916, 2901, 2874 (CH); 2777w; 1699s (C=O); 1476; 1101.

Acc. Mass spectrometry: calculated=198.1130 ($MH^+$); found=198.1130.

Example 2

Preparation of 3-phenylmorpholin-4-ol

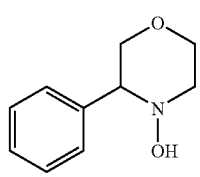

[P1]

Activated $MnO_2$ (0.65 g, 7.41 mmol) was added to a solution of N-hydroxymorpholine (0.25 g, 2.47 mmol) in dichloromethane (15 mL) at 0° C. and the mixture was stirred for 1 h. The reaction mixture was filtered through a pad of Celite™ and $Na_2SO_4$. The filtrate was added dropwise to a solution of phenylmagnesium chloride (2.0 M in tetrahydrofuran, 2.47 mL, 4.94 mmol) at −10° C. The reaction mixture was stirred at 0° C. for 0.5 h and then saturated aqueous ammonium chloride solution (15 mL) and dichloromethane (15 mL) were added. The aqueous phase was separated and extracted with dichloromethane (2×20 mL). The combined organic layers were dried ($Na_2SO_4$) and concentrated under reduced pressure. The crude product was subjected to flash chromatography on $SiO_2$ eluting with 25% diethyl ether in hexanes to give the title compound (0.045 g, 11%) as a white crystalline solid.

$v_{max}$(Nujol™ mull)/cm$^{-1}$ 3201 (br., O—H), 1104 (s, C—O)

$\delta_H$ (300 MHz): 7.22 (m, 5H), 3.85 (d, 1H, J=10.5 Hz), 3.72-3.50 (m, 3H), 3.31 (t, 1H, J=10.5 Hz), 3.12 (d, 1H, J=10.5 Hz), 2.81 (td, 1H, $J_1$=11.2 Hz, $J_2$=3.4 Hz).

$\delta_C$ (75.5 MHz): 138.1 (0), 128.6 (1), 127.9 (1), 72.45 (2), 72.16 (1), 66.78 (2), 57.67 (2).

HRMS (electrospray mode): m/z=180.1026710 (MH$^+$) (calc. 180.1019051).

Example 3

Preparation of 3-benzylmorpholin-4-ol [P2]

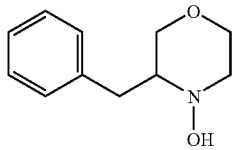

[P2]

Activated $MnO_2$ (1.29 g, 14.8 mmol) was added to a solution of N-hydroxymorpholine (0.50 g, 4.95 mmol) in dichloromethane (25 mL) at 0° C. and the mixture was stirred for 1 h. The reaction mixture was filtered through a pad of Celite™ and $Na_2SO_4$. The filtrate was added dropwise to a solution of benzylmagnesium chloride (2.0 M in tetrahydrofuran, 4.95 mL, 9.90 mmol) at −10° C. The reaction mixture was stirred at 0° C. for 0.5 h and then saturated aqueous ammonium chloride solution (25 mL) and dichloromethane (25 mL) were added. The aqueous phase was separated and extracted with dichloromethane (2×30 mL). The combined organic layers were dried ($Na_2SO_4$) and concentrated under reduced pressure. The crude product was subjected to flash chromatography on $SiO_2$ eluting with 25% diethyl ether in hexanes to give the title compound (0.326 g, 34%) as a white crystalline solid.

$v_{max}$(Nujol™ mull)/cm$^{-1}$ 3203 (br., O—H), 1107 (s, C—O).

$\delta_H$ (300 MHz): 7.23 (m, 5H), 3.89 (d, 1H, J=11.7 Hz), 3.74-3.56 (m, 2H), 3.44 (d, 1H, J=13.0 Hz), 3.23 (m, 2H), 2.87 (m, 2H), 2.39 (t, 1H, J=10.5 Hz).

$\delta_C$ (75.5 MHz): 137.7 (0), 129.2 (1), 128.5 (1), 126.4 (1), 70.22 (2), 67.76 (1), 66.60 (2), 58.60 (2), 35.85 (1).

HRMS (electrospray mode)=194.1186060 (MH$^+$) (calc. 194.1175552).

Example 4

Preparation of 3-cyclohexylmorpholin-4-ol

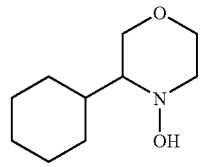

[P3]

Activated $MnO_2$ (1.29 g, 14.8 mmol) was added to a solution of N-hydroxymorpholine (0.50 g, 4.95 mmol) in dichloromethane (25 mL) at 0° C. and the mixture was stirred for 1 h. The reaction mixture was filtered through a pad of Celite™ and $Na_2SO_4$. The filtrate was added dropwise to a solution of cyclohexylmagnesium chloride (2.0 M in diethyl ether, 4.95 mL, 9.90 mmol) at −10° C. The reaction mixture was stirred at 0° C. for 0.5 h and then saturated aqueous ammonium chloride solution (25 mL) and dichloromethane (25 mL) were added. The aqueous phase was separated and extracted with dichloromethane (2×30 mL). The combined organic layers were dried ($Na_2SO_4$) and concentrated under reduced pressure. The crude product was subjected to flash chromatography on $SiO_2$ eluting with 50% diethyl ether in hexanes to give the title compound (0.220 g, 24%) as a white crystalline solid.

$v_{max}$(Nujol™ mull)/cm$^{-1}$ 3203 (br., O—H), 1107 (s, C—O).

$\delta_H$ (300 MHz): 3.84 (m, 1H), 3.55 (t, 1H, J=11.3 Hz), 3.17 (d, 1H, J=10.5 Hz), 2.79 (t, 1H, J=10.5 Hz), 2.46 (d, 1H, J=9.8 Hz), 2.06-1.45 (m, 6H), 1.35-0.82 (m, 6H).

$\delta_C$ (75.5 MHz): 70.83 (1), 67.42 (2), 66.29 (2), 58.84 (2), 36.71 (1), 30.14 (2), 27.64 (2), 26.96 (2), 26.75 (2).

HRMS (electrospray mode)=186.1496690 (MH$^+$) (calc. 186.1488553).

Example 5

Preparation of 3-cyclopentylmorpholin-4-ol

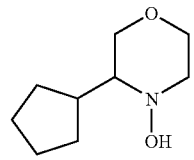

[P4]

Activated $MnO_2$ (1.29 g, 14.8 mmol) was added to a solution of N-hydroxymorpholine (0.50 g, 4.95 mmol) in dichloromethane (25 mL) at 0° C. and the mixture was stirred for 1 h. The reaction mixture was filtered through a pad of Celite™ and $Na_2SO_4$. The filtrate was added dropwise to a solution of cyclopentylmagnesium chloride (2.0 M in diethyl ether, 4.95 mL, 9.90 mmol) at −10° C. The reaction mixture was stirred at 0° C. for 0.5 h and then saturated aqueous ammonium chloride solution (25 mL) and dichloromethane (25 mL) were added. The aqueous phase was separated and extracted with dichloromethane (2×30 mL). The combined organic layers were dried (Na$_2$SO$_4$) and concentrated under reduced pressure. The crude product was subjected to flash chromatography on SiO$_2$ eluting with 70% diethyl ether in hexanes to give the title compound (0.246 g, 29%) as a white crystalline solid.

$\nu_{max}$(Nujol™ mull)/cm$^{-1}$ 3233 (br., O—H), 1118 (s, C—O).

$\delta_H$ (300 MHz): 3.90 (t, 2H, J=9.9 Hz), 3.55 (t, 1H, J=10.7 Hz), 3.30 (t, 1H, J=10.3 Hz), 3.15 (d, 1H, J=11.1 Hz), 2.80 (t, 1H, J=10.4 Hz), 2.57 (m, 1H), 2.19 (m, 1H), 1.89 (m, 1H), 1.73-1.02 (m, 7H)

$\delta_C$ (75.5 MHz): 69.31 (1), 67.91 (2), 65.65 (2), 57.83 (2), 39.91 (1), 30.80 (2), 28.19 (2), 24.89 (2).

HRMS (electrospray mode)=172.1327720 (MH$^+$) (calc. 172.1332052)

Example 6

Preparation of 2-phenylpiperidin-1-ol

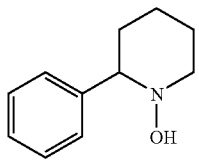
[P5]

Activated MnO$_2$ (1.29 g, 14.8 mmol) was added to a solution of N-hydroxypiperidine (0.50 g, 4.95 mmol) in dichloromethane (25 mL) at 0° C. and the mixture was stirred for 1 h. The reaction mixture was filtered through a pad of Celite™ and Na$_2$SO$_4$. The filtrate was added dropwise to a solution of phenylmagnesium chloride (2.0 M in tetrahydrofuran, 4.95 mL, 9.90 mmol) at −10° C. The reaction mixture was stirred at 0° C. for 0.5 h and then saturated aqueous ammonium chloride solution (25 mL) and dichloromethane (25 mL) were added. The aqueous phase was separated and extracted with dichloromethane (2×30 mL). The combined organic layers were dried (Na$_2$SO$_4$) and concentrated under reduced pressure. The crude product was subjected to flash chromatography on SiO$_2$ eluting with 30% diethyl ether in hexanes to give the title compound (0.330 g, 38%) as a white crystalline solid.

$\nu_{max}$(Nujol™ mull)/cm$^{-1}$ 3204 (br., O—H).

$\delta_H$ (300 MHz): 7.30 (m, 5H), 3.34 (m, 2H), 2.59 (t, 1H, J=11.0 Hz), 1.87-1.50 (m, 3H), 1.36 (m, 1H).

$\delta_C$ (75.5 MHz): 143.4 (0), 128.4 (1), 127.4 (1), 127.1 (1), 73.51 (1), 58.94 (2), 35.21 (2), 25.83 (2), 24.07 (2).

HRMS (electrospray mode)=178.1223660 (MH$^+$) (calc. 178.1226406).

Example 7

Preparation of 2-benzylpiperidin-1-ol

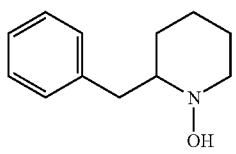
[P6]

Activated MnO$_2$ (1.29 g, 14.8 mmol) was added to a solution of N-hydroxypiperidine (0.50 g, 4.95 mmol) in dichloromethane (25 mL) at 0° C. and the mixture was stirred for 1 h. The reaction mixture was filtered through a pad of Celite™ and Na$_2$SO$_4$. The filtrate was added dropwise to a solution of benzylmagnesium chloride (2.0 M in tetrahydrofuran, 4.95 mL, 9.90 mmol) at −10° C. The reaction mixture was stirred at 0° C. for 0.5 h and then saturated aqueous ammonium chloride solution (25 mL) and dichloromethane (25 mL) were added. The aqueous phase was separated and extracted with dichloromethane (2×30 mL). The combined organic layers were dried (Na$_2$SO$_4$) and concentrated under reduced pressure. The crude product was subjected to flash chromatography on SiO$_2$ eluting with 60% diethyl ether in hexanes to give the title compound (0.309 g, 33%) as a white crystalline solid.

$\nu_{max}$(Nujol™ mull)/cm$^{-1}$ 3212 (br., O—H).

$\delta_H$ (300 MHz): 7.24 (m, 5H), 3.65 (d, 1H, J=10.5 Hz), 3.40 (d, 1H, J=10.4 Hz), 2.66-2.48 (m, 2H), 2.40 (t, 1H, J=11.2 Hz), 1.79-1.48 (m, 4H), 1.26-1.00 (m, 2H).

$\delta_C$ (75.5 MHz): 139.3 (0), 129.6 (1), 128.2 (1), 126.0 (1), 69.28 (1), 59.78 (2), 39.95 (2), 30.62 (2), 25.92 (2), 23.53 (2).

HRMS (electrospray mode)=192.1377940 (MH$^+$) (calc. 192.1382906).

Example 8

Preparation of 2-cyclohexylpiperidin-1-ol

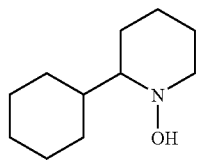

Activated MnO$_2$ (1.29 g, 14.8 mmol) was added to a solution of N-hydroxypiperidine (0.50 g, 4.95 mmol) in dichloromethane (25 mL) at 0° C. and the mixture was stirred for 1 h. The reaction mixture was filtered through a pad of Celite™ and Na$_2$SO$_4$. The filtrate was added dropwise to a solution of cyclohexylmagnesium chloride (2.0 M in diethyl ether, 4.95 mL, 9.90 mmol) at −10° C. The reaction mixture was stirred at 0° C. for 0.5 h and then saturated aqueous ammonium chloride solution (25 mL) and dichloromethane (25 mL) were added. The aqueous phase was separated and extracted with dichloromethane (2×30 mL). The combined organic layers were dried (Na$_2$SO$_4$) and concentrated under reduced pressure. The crude product was subjected to flash chromatography on SiO$_2$ eluting with 40% diethyl ether in hexanes to give the title compound (0.241 g, 27%) as a white crystalline solid.

$\nu_{max}$(Nujol™ mull)/cm$^{-1}$ 3195 (br., O—H).

$\delta_H$ (300 MHz): 3.32 (d, 1H, J=10.9 Hz), 2.49 (t, 1H, J=11.7 Hz), 2.16 (d, 1H, J=10.4 Hz), 2.04 (t, 1H, J=12.2 Hz), 1.84-0.90 (m, 16H).

$\delta_C$ (75.5 MHz): 72.55 (1), 60.27 (2), 38.03 (1), 30.36 (2), 27.07 (2), 26.97 (2), 26.69 (2), 25.73 (2), 23.92 (2).

HRMS (electrospray mode) 184.1690950 (MH$^+$) (calc. 184.1695908).

Example 9

2,6-dimethyl-3-phenylmorpholin-4-ol

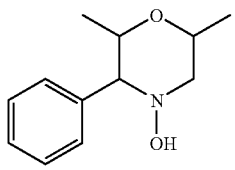

9.1. Preparation of 1-hydroxy-2,6-dimethylmorpholine 2,6-Dimethylmorpholine (26.74 mL, 0.22 mmol) was cooled to 0° C. and hydrogen peroxide (32.2 mL, 27.5%, 0.26 mmol) was added as drops with stirring. The solution was stored for six hours at 0° C. (danger of exotherm). The product was extracted into ether and the organic phase was separated dried (magnesium sulfate) and concentrated. Chromatography on silica gel using ether petrol (7:3) as the eluent gave the product (17%) as mixture of syn and anti diastereoisomers, which was used immediately in the preparation of the nitrone.

9.2. Preparation of 2,6-dimethyl-3-phenylmorpholin-4-ol

Activated $MnO_2$ (0.50 g, 1.91 mmol) was added to a solution of 1-hydroxy-2,6-dimethylmorpholine (0.25 g, 5.72 mmol) in dichloromethane (15 mL) at 0° C. and the mixture was stirred for 1 h. The reaction mixture was filtered through a pad of Celite™ and $Na_2SO_4$. The filtrate was added dropwise to a solution of phenylmagnesium chloride (2.0 M in tetrahydrofuran, 1.91 mL, 3.82 mmol) at –10° C. The reaction mixture was stirred at 0° C. for 0.5 h and then saturated aqueous ammonium chloride solution (15 mL) and dichloromethane (15 mL) were added. The aqueous phase was separated and extracted with dichloromethane (2×20 mL). The combined organic layers were dried ($Na_2SO_4$) and concentrated under reduced pressure. The crude product was subjected to flash chromatography on $SiO_2$ eluting with 60% diethyl ether in hexanes to give the title compound (0.11 g, 28%) as a white crystalline solid.

$v_{max}$(Nujol™ mull)/cm$^{-1}$ 3325 (br., O—H).

$\delta_H$ (300 MHz): 7.59 (m, 2H), 7.36 (m, 3H), 4.22 (s, 1H), 4.00 (m, 2H), 2.86 (m, 2H), 1.31 (d, 3H, J=6.2 Hz), 1.12 (d, 3H, J=6.6 Hz).

$\delta_C$ (75.5 MHz): 132.2 (1), 127.9 (1), 127.8 (1), 70.72 (1), 69.92 (1), 56.57 (2), 19.05 (3), 18.36 (3).

HRMS (electrospray mode)=208.1332052 (MH$^+$) (calc. 208.1329280).

Example 10

Anxiolytic Activity—Black and White Box Test

The anxiolytic effect of the compound of Example 1 (Abio 09/01) was compared with that of the marketed anxiolytic drug, diazepam, and the corresponding compound of formula (A), namely cis-1,2,3,4,5,6a,7,8,9,10a,10b-dodeca-1,4-oxazino-[3',4':2,3]benzo[d]isoxazol-4-one (hereinafter referred to as Comparative Compound A). In this test model, the effect of a stressful stimulus on the exploratory behaviour of mice receiving a control or a therapeutic amount of one of the compounds referred to in Table 1 was investigated.

TABLE 1

| Group | No. of animals | Substance | Dose |
|---|---|---|---|
| 1 | 10 | Vehicle | 0 |
| 2 | 10 | Diazepam | 1.25 mg/kg |
| 3 | 10 | Comparative Compound A | 0.1 mg/kg |
| 4 | 10 | Ex. 1 (Abio 09/01) | 0.1 mg/kg |

The black and white box comprised a Plexiglas open-topped box (45×27×27 cm high) positioned on a bench 86.5 cm above the floor level in a dark and quiet room. The test box was divided into two compartments (ratio 2:3) by a partition (height 60 cm). Two fifths (⅖) of the box was painted lack and illuminated with a red light (4×15 W; 10 lux); the remainder of the box was painted white and illuminated with a 60 W (400 lux) light source. The red and white lights are positioned 17 cm above the box. The partition is black on the side facing the black compartment and white on the side facing the white compartment. The compartments are connected by a 7.5 cm×7.5 cm opening in the centre bottom of the partition. The floor of the white compartment is divided into nine fields, and the floor of the black compartment is divided into six fields. The test room is separated into two parts by a black curtain. The drug treatment takes place in one part of the room using a minimum red light; the other part of the room, without lights, contains the test system.

In this test system, normal animals show a preference for exploration, measured as rearing behaviour, line crossing and time spent in the black section as a consequence of the aversive properties of the brightly lit white area. The characteristic action of anxiolytic agents from the benzodiazepine series is to disinhibit the suppressed behaviour, causing a redistribution of exploratory activity in the white section. Black and white box tests have been validated in mice, which are the more suitable species for this procedure (Costall et al, *Pharm. Bioch. & Behaviour*, 32, 777-785 (1989)).

Naïve BKW male albino mice of 30 to 35 g were used in all studies. 10 mice were normally housed in each cage and kept for at least two weeks on a 12 hour light/dark cycle with lights off at 07.00 h. Behavioural testing was conducted between 13.00 and 18.00 h in a darkened room illuminated with red light. Mice were taken from the dark holding room to the testing room in an enclosed trolley and allowed at least 1 h for adaptation to the new environment.

The animals each receive a control or an active agent intraperitoneally 40 minutes before testing. At the start of the test the mice are placed into the white section of the box, facing the wall opposite to the partition and their behaviour is recorded by remote video over a 5-minute experimental period.

The results are shown in Table 2 below, wherein TB=time in white section; FI=Initial potency; PT=Total passages through the partition; $A_{tot}$=Total exploratory activity; $C_{tot}$=total number of crossings; $R_{tot}$=Total number of rearings; RB/TB=rearings in the white compartment/time in white; CB/TB=crossings in the white compartment/time in white; RN/TN=rearings in the black compartment/time in black; CN/TN=crossings in the black compartment/time in black.

TABLE 2

|     | Diazepam 1.25 mg/kg | Ex. 1 (Abio 09/01) 0.1 mg/kg | Comparative Compound A 0.1 mg/kg |
| --- | --- | --- | --- |
| TB | +33.2 | +53.4 | +52.1 |
| FI | +12.7 | +11.5 | +8.1 |
| PT | +1.5 | +0.9 | +4.1 |
| $A_{tot}$ | +46.7 | +10.4 | +53.7 |
| $C_{tot}$ | +30.7 | +7.5 | +19.1 |
| $R_{tot}$ | +21.2 | +5 | +23.9 |
| RB/TB | +0.06 | +0.02 | +0.04 |
| RN/TN | +0.09 | +0.06 | +0.13 |
| CB/TB | +0.08 | −0.05 | +0.01 |
| CN/TN | +0.1 | 0.08 | +0.08 |

Example 11

Anxiolytic Activity—Elevated Plus Maze in Rats

The X-maze is constructed from Perspex® and comprises four arms (2 open, 2 closed), each 50 cm long by 9.5 wide and 40 high (closed arms only) connected by a centre square (9.5×9.5). The open arm has a small lip (3 mm) to assist in the retention of the rat on the arm. The apparatus was housed in a room under subdued lighting conditions.

This model is based on the observation of spontaneous activity of rodents placed in an aversive environment produced by height and often spaces. The open arms evoke more fears, and this results in less exploration. Anxiolytic drugs increase the exploratory activity and the number of entries into the open arms. Rats were allowed at least 1 hour to acclimatise to the environment before testing commenced. Drug treatments were given IP in a pseudo-random, blind design, 40 minutes before behavioural testing, as appropriate. Rats were placed onto the centre square of the X-maze facing a specified open arm, and its behaviour was recorded by remote video over a 5 minute experimental period. The behavioural parameters were subsequently assessed by technicians reviewing the videotape and included: entries into each arm type, time spent on each arm type, rearing, stretch attend postures and head dips. The results are shown in Table 3 below.

TABLE 3

| In open arms | Vehicle | Diazepam | Comparative Compound A 0.125 mg/kg | Ex. 1 (Abio 09/01) 0.125 mg/kg |
| --- | --- | --- | --- | --- |
| % time spent | 11 ± 4% | 25 ± 5% | 21 ± 11% | 39 ± 10% |
| No. of entries | 1.8 ± 0.5 | 4 ± 0.6 | 3 ± 1.1 | 5.2 ± 1.4 |

Example 12

Antidepressant Activity

The "escape deficit" test that derives from the classic paradigm of "learned helplessness" was used, as described by Meloni et al. in *Pharmacol. Biochem. Behav.* 46, 423-6 (1993) and Gambarana et al. in *Behav. Pharmacol.* 6, 66-73 (1995) and *Neuropsychopharmacol.* 21, 247-57 (1999). Exposure to an unavoidable stress induces hyperactive behaviour, which, after 24 hours, makes the rats unable to escape from a nociceptive stimulus. Rats exposed to unavoidable stress make 0-5 escapes out of 30 trials, while naïve rats realise 26-30 escapes. Classical anti-depressives prevent the occurrence of the escape deficit after chronic treatment (15 days).

Rats were treated intra-peritoneally (IP) for 15 days, and then submitted to the unavoidable stress (16 hours after the last dosing) prior to being subjected to the escape test (24 hours after the last dosing). The results are shown in Table 4 below.

TABLE 4

| Treatment | No. of escapes |
| --- | --- |
| Naïve | 24.2 ± 0.9 |
| Vehicle | 1.7 ± 0.4 |
| Comparative Compound A | 3.5 ± 0.9 |
| Ex. 1 (Abio 09/01) | 23.3 ± 1.3 |

Examples 10-12

Conclusions

From these results can be seen that, although the anxiolytic effects of the compound of this invention and the comparative prior art compound (being compounds of the same class) are similar, the success of the compound of the invention in the test for antidepressant activity is significantly greater than that of the comparative prior art compound. In the results reported here, the compound of the invention results in bringing the animal's behaviour back to the level of naïve animals (who had not been subjected to the unavoidable stress).

Example 13

Antidepressant Activity—Despair and Open Field Tests

Rats treated with the compound of Example 1 were compared to either rats treated with the classical antidepressant, clomipramine or controls in the despair test (forced swim). The same groups were also tested for the reserpine-induced changes in open field behaviour.

13.1. Animals

Male rats of the Wistar strain (purchased from Charles River, Italy) weighing 220-240 g were used throughout all experiments. For at least 1 week prior to the experiment, the rats were housed four to a cage at a constant temperature of 21° C., and under a 12-h light/dark cycle (lights on between 08:00 and 20:00), with food and water available ad libitum.

13.2. Drugs and Treatment

A group of animals received a treatment with clomipramine hydrochloride (50 and 100 mg/kg). The drug, purchased by Sigma (USA), were freshly diluted in physiological saline and injected intraperitoneally (IP). Rats subjected to the despair test received three such injections 24, 5 and 1 hour prior to behavioural test. Physiological saline (saline) was injected IP to control animals. The compound of Example 1 (0.2 and 0.5 mg/kg) was injected IP to a group of rats.

An acute IP injection of clomipramine hydrochloride (50 mg/kg) or of the compound of Example 1 (0.2 and 0.5 mg/kg) or physiological saline was made in animals subjected to the reserpine-induced changes in the open field test (the injection was made together with the last reserpine administration, e.g. 1 h prior to the open field test).

All animals were gently manipulated by experienced facilities' keepers avoiding any environmental or physical stress. Rats subjected to drugs or physiological saline administration received an injection of a 1-mL standard volume of solution with a 23-gauge stainless steel needle of 31 mm length (for IP injections) or 21 mm length (for SC injections). The animals were randomly assigned to any treatment group and were used only once in the behavioural experiments.

13.3. Behavioural Tests

For the despair test, rats were individually forced to swim inside vertical Plexiglas cylinders containing 15 cm of water maintained at 25° C. (*Nature* 266: 730-732, Porsolt et al., 1977). After 15 min in the water they were removed and allowed to dry for 15 min in a heated container before being returned to their home cages. They were replaced in the cylinders 24 h later and the total duration of immobility was measured during a 5-min test. A rat was judged to be immobile whenever it remained passively floating in the water in a slightly hunched but upright position, its head just above the surface.

Reserpine-induced changes in open field behaviour was studied according to the method described in *Naunyn-Schmiedeberg's Arch. Pharmacol.* 293: 109-114 (Vetulani et al., 1976). Reserpine (Sigma, USA) was dissolved in physiological saline and injected daily for 14 days at the dose of 0.1 mg/kg subcutaneously (SC). A period of 1 hour after the last injection of reserpine, animals were subjected to the open field test. This consisted of the measure of ambulation and rearing of the rat in a circular area divided into 17 equal sections and lighted by a centrally suspended lamp. The areas explored by the rat at least with anterior paws was recorded in 5 min test. The episodes of rearing towards the centre or the walls were also recorded in 5 min test.

13.4. Statistical Analysis

All data were analysed using univariate random design analysis of variance (one-way ANOVA) and the post hoc Dunnett's test for multiple comparisons. A P-value of 0.05 or less was considered as indicative of a significant difference. Where not indicated, one-way ANOVA revealed no significant level of variance.

The duration of immobility in the despair test (forced swim) in rats injected with physiological saline as placebo, with clomipramine 50 mg/kg or with the compound of Example 1 (0.2 and 05 mg/kg) are shown in Table 5.

TABLE 5

| Treatment | Duration of Immobility |
|---|---|
| Placebo (6) | 167.60 ± 9.44 |
| Clomipramine 50 mg/kg (4) | 105.95 ± 9.13* |
| Ex. 1 (Abio 09/01), 0.2 mg/kg (6) | 167.00 ± 11.11 |
| Ex. 1 (Abio 09/01), 0.5 mg/kg (6) | 109.83 ± 9.12* |

Values are mean ± S.E.M. In parentheses the number of animals per each group is indicated.
*Significantly different as compared to placebo-treated controls (p < 0.05, Dunnett's test for multiple comparisons).

The number of floor units and rearing episodes in rats injected with physiological saline as placebo, with clomipramine 50 mg/kg or with the compound of Example 1 (0.2 and 05 mg/kg).

The number of floor units and rearing episodes in rats injected with physiological saline as placebo, with clomipramine 50 mg/kg or with the compound of Example 1 (0.2 and 05 mg/kg) are shown in Table 6.

TABLE 6

| Treatment | No. of Floor Units | Rearing Episodes |
|---|---|---|
| Reserpine + placebo (12) | 131.3 ± 12.1 | 6.4 ± 0.2 |
| Reserpine + clomipramine 50 mg/kg (7) | 84.6 ± 8.1* | 2.4 ± 0.2* |
| Ex. 1 (Abio 09/01), 0.2 mg/kg (12) | 128.1 ± 11.9 | 5.9 ± 0.3 |
| Ex. 1 (Abio 09/01), 0.5 mg/kg (12) | 92.2 ± 11.1* | 2.2 ± 0.5* |

Values are mean ± S.E.M. In parentheses the number of animals per each group is indicated. One-way ANOVA revealed no significant level of variance for treatment for "number of floor units" [$F_{(3,29)} = 2.27$ ($p < 0.10$)] and for "rearing episodes" [$F_{(3,29)} = 2.10$ ($p < 0.10$)].
*Significantly different as compared to reserpine + placebo controls (p < 0.05, Dunnett's test for multiple comparisons).

13.5. Results and Conclusions

These results show that rats treated with the compound of Example 1 at 0.5 mg/kg exhibit a significant decrease of immobility time in the despair test in comparison to the control group. This effect was similar to that of rats treated with clomipramine 50 mg/kg.

Open field performance in the reserpine test revealed a decreased ambulation (number of floor units entered) and rearing (number of episodes) for those rats that were treated with the compound of Example 1 at 0.5 mg/kg in comparison to the control group. These effects were similar to those of rats treated with clomipramine 50 mg/kg.

Example 14

Anxiolytic Activity—Black and White Box Test

Further studies were conducted comparing the anxiolytic effect of the compound of Example 1 and the compounds of Example 2-7 [Compounds P1-P6] with that of the marketed anxiolytic drug, diazepam, and the corresponding compound of formula (A) (Comparative Compound A).

In the black/white test system (B/W box) normal animals showed a preference for remaining in the less aversive compartment, measured as time spent in black section, as well as for exploration, measured as rearing behaviour and line crossings, as a consequence of the aversive properties of the brightly lit. The characteristic action of anxiolytic agents is to cause a redistribution of exploratory activity and time spent in the white section.

Each mouse was placed into the centre of the white, brightly lit area backing the opening between the B/W compartments. Animals behaviour was recorded by a remote video camera for 5 minutes. The recordings were subsequently evaluated on the TV by two operators unaware of drug treatment. The following behavioural parameters were recorded:
a) the latency of the initial movement from the white to the black area: L (sec);
b) the time spent in the white area TW (sec); the time spent in the black area is calculated by the difference: 5−TW=TB (sec);
c) the number of transitions between the two compartments T (No./5 min);
d) the total activity in the white and black compartments, $A_{tot}$ (No./5 min);
e) the total activity in the white area throughout the time spent in the white area: $A_{tot}W/TW$ (No./sec);
f) the total activity in the black area throughout the time spent in the black area: $A_{tot}B/TB$ (No./sec);
g) the total number of exploratory rearings: $R_{tot}$ (No./5 min);
h) the total number of line crossings: $C_{tot}$ (No./5 min);

i) the number of exploratory rearings in the white section RW/TW (No./sec);
j) the number of line crossings in the white section CW/TW (No./sec).

Treatment Was:

1 Vehicle 0
2 Diazepam 1.25 mg/kg
3 Comparative Compound A 0.1 mg/kg
4 compound of Example 1, 0.1 mg/kg
5 P1 0.1 mg/kg
6 P2 0.1 mg/kg
7 P3 0.1 mg/kg
8 P4 0.1 mg/kg
9 P5 0.1 mg/kg
10 P6 0.1 mg/kg Each group was composed by 8 animals.
Results are shown in the following tables.

| Parameter 1: Latency L (sec) | | | | |
|---|---|---|---|---|
| | Animals | Mean | SD | SE |
| Vehicle CMC | 5.000 | 16.200 | 10.2320 | 4.576 |
| Diazepam 1.25 mg/kg | 8.000 | 13.750 | 6.8400 | 2.418 |
| P1 0.1 mg/kg | 8.000 | 20.125 | 15.5880 | 5.511 |
| P2 0.1 mg/kg | 8.000 | 19.625 | 8.4340 | 2.982 |
| P5 0.1 mg/kg | 8.000 | 20.625 | 8.2620 | 2.921 |
| P6 0.1 mg/kg | 8.000 | 14.500 | 6.6550 | 2.353 |

L: ANOVA comparison was not significant

| Parameter 2: Time spent in White area (TW)(sec) | | | | |
|---|---|---|---|---|
| | Animals | Mean | SD | SE |
| Vehicle CMC | 5 | 74.200 | 49.7770 | 22.261 |
| Diazepam 1.25 mg/kg | 8 | 97.750 | 61.9860 | 21.915 |
| P1 0.1 mg/kg | 8 | 116.750 | 52.7140 | 18.637 |
| P2 0.1 mg/kg | 8 | 59.250 | 39.0340 | 13.801 |
| P5 0.1 mg/kg | 8 | 105.125 | 40.6360 | 14.367 |
| P6 0.1 mg/kg | 8 | 152.125 | 37.1580 | 13.137 |

| TW: ANOVA comparison (S = significant) | | |
|---|---|---|
| | P-value | |
| Vehicle CMC, Diazepam 1.25 mg/kg | .3902 | |
| Vehicle CMC, P1 0.1 mg/kg | .1245 | |
| Vehicle CMC, P2 0.1 mg/kg | .5844 | |
| Vehicle CMC, P5 0.1 mg/kg | .2608 | |
| Vehicle CMC, P6 0.1 mg/kg | .0065 | S |
| Diazepam 1.25 mg/kg, P1 0.1 mg/kg | .4290 | |
| Diazepam 1.25 mg/kg, P2 0.1 mg/kg | .1134 | |
| Diazepam 1.25 mg/kg, P5 0.1 mg/kg | .7580 | |
| Diazepam 1.25 mg/kg, P6 0.1 mg/kg | .0277 | S |
| P1 0.1 mg/kg, P2 0.1 mg/kg | .0203 | S |
| P1 0.1 mg/kg, P5 0.1 mg/kg | .6275 | |
| P1 0.1 mg/kg, P6 0.1 mg/kg | .1447 | |
| P2 0.1 mg/kg, P5 0.1 mg/kg | .0609 | |
| P2 0.1 mg/kg, P6 0.1 mg/kg | .0004 | S |
| P5 0.1 mg/kg, P6 0.1 mg/kg | .0551 | |

| Parameter 3: Transitions/5 min (T) | | | | |
|---|---|---|---|---|
| | Animals | Mean | SD | SE |
| Vehicle CMC | 5.000 | 9.600 | 6.4650 | 2.891 |
| Diazepam 1.25 mg/kg | 8.000 | 13.375 | 9.3490 | 3.306 |
| P1 0.1 mg/kg | 8.000 | 19.500 | 10.8630 | 3.841 |
| P2 0.1 mg/kg | 8.000 | 10.000 | 9.5320 | 3.370 |
| P5 0.1 mg/kg | 8.000 | 14.750 | 7.3050 | 2.583 |
| P6 0.1 mg/kg | 8.000 | 24.250 | 11.2220 | 3.968 |

| T: ANOVA comparison | | |
|---|---|---|
| | P-value | |
| Vehicle CMC, Diazepam 1.25 mg/kg | .4885 | |
| Vehicle CMC, P1 0.1 mg/kg | .0743 | |
| Vehicle CMC, P2 0.1 mg/kg | .9413 | |
| Vehicle CMC, P5 0.1 mg/kg | .3459 | |
| Vehicle CMC, P6 0.1 mg/kg | .0098 | S |
| Diazepam 1.25 mg/kg, P1 0.1 mg/kg | .2033 | |
| Diazepam 1.25 mg/kg, P2 0.1 mg/kg | .4801 | |
| Diazepam 1.25 mg/kg, P5 0.1 mg/kg | .7730 | |
| Diazepam 1.25 mg/kg, P6 0.1 mg/kg | .0271 | S |
| P1 0.1 mg/kg, P2 0.1 mg/kg | .0517 | |
| P1 0.1 mg/kg, P5 0.1 mg/kg | .3219 | |
| P1 0.1 mg/kg, P6 0.1 mg/kg | .3219 | |
| P2 0.1 mg/kg, P5 0.1 mg/kg | .3219 | |
| P2 0.1 mg/kg, P6 0.1 mg/kg | .0046 | S |
| P5 0.1 mg/kg, P6 0.1 mg/kg | .0517 | |

| Parameter 4: Total Activity: $A_{tot}$ (No./5 min) | | | | |
|---|---|---|---|---|
| | Animals | Mean | SD | SE |
| Vehicle CMC | 5.000 | 112.400 | 49.1710 | 21.990 |
| Diazepam 1.25 mg/kg | 8.000 | 213.125 | 90.5810 | 32.025 |
| P1 0.1 mg/kg | 8.000 | 197.375 | 47.7670 | 16.888 |
| P2 0.1 mg/kg | 8.000 | 168.625 | 53.6020 | 18.951 |
| P5 0.1 mg/kg | 8.000 | 197.000 | 37.8490 | 13.382 |
| P6 0.1 mg/kg | 8.000 | 229.375 | 42.1660 | 14.908 |

| $A_{tot}$: ANOVA comparison | | |
|---|---|---|
| | P-value | |
| Vehicle CMC, Diazepam 1.25 mg/kg | .0035 | S |
| Vehicle CMC, P1 0.1 mg/kg | .0123 | S |
| Vehicle CMC, P2 0.1 mg/kg | .0902 | |
| Vehicle CMC, P5 0.1 mg/kg | .0126 | S |
| Vehicle CMC, P6 0.1 mg/kg | .0008 | S |
| Diazepam 1.25 mg/kg, P1 0.1 mg/kg | .5821 | |
| Diazepam 1.25 mg/kg, P2 0.1 mg/kg | .1250 | |
| Diazepam 1.25 mg/kg, P5 0.1 mg/kg | .5732 | |
| Diazepam 1.25 mg/kg, P6 0.1 mg/kg | .5702 | |
| P1 0.1 mg/kg, P2 0.1 mg/kg | .3173 | |
| P1 0.1 mg/kg, P5 0.1 mg/kg | .9895 | |
| P1 0.1 mg/kg, P6 0.1 mg/kg | .2664 | |
| P2 0.1 mg/kg, P5 0.1 mg/kg | .3236 | |
| P2 0.1 mg/kg, P6 0.1 mg/kg | .0386 | S |
| P5 0.1 mg/kg, P6 0.1 mg/kg | .2610 | |

Parameter 5: Total Activity in white area: $A_{tot}W/TW$ (No./sec)

| | Animals | Mean | SD | SE |
|---|---|---|---|---|
| Vehicle CMC | 5.000 | .475 | .1800 | .080 |
| Diazepam 1.25 mg/kg | 8.000 | .723 | .3030 | .107 |
| P1 0.1 mg/kg | 8.000 | .608 | .2980 | .105 |
| P2 0.1 mg/kg | 8.000 | .519 | .2530 | .089 |
| P5 0.1 mg/kg | 8.000 | .571 | .1570 | .055 |
| P6 0.1 mg/kg | 8.000 | .705 | .1380 | .049 |

$A_{tot}W/TW$: ANOVA comparison was not significant

Parameter 6: Total Activity in black area: $A_{tot}B/TB$ (No./sec)

| | Animals | Mean | SD | SE |
|---|---|---|---|---|
| Vehicle CMC | 5.000 | .341 | .1450 | .065 |
| Diazepam 1.25 mg/kg | 8.000 | .723 | .3190 | .113 |
| P1 0.1 mg/kg | 8.000 | .652 | .1380 | .049 |
| P2 0.1 mg/kg | 8.000 | .571 | .1840 | .065 |
| P5 0.1 mg/kg | 8.000 | .708 | .1530 | .054 |
| P6 0.1 mg/kg | 8.000 | .835 | .1750 | .062 |

$A_{tot}B/TB$: ANOVA comparison

| | P-value | |
|---|---|---|
| Vehicle CMC, Diazepam 1.25 mg/kg | .0017 | S |
| Vehicle CMC, P1 0.1 mg/kg | .0091 | S |
| Vehicle CMC, P2 0.1 mg/kg | .0496 | S |
| Vehicle CMC, P5 0.1 mg/kg | .0025 | S |
| Vehicle CMC, P6 0.1 mg/kg | <.0001 | S |
| Diazepam 1.25 mg/kg, P1 0.1 mg/kg | .4832 | |
| Diazepam 1.25 mg/kg, P2 0.1 mg/kg | .1351 | |
| Diazepam 1.25 mg/kg, P5 0.1 mg/kg | .8796 | |
| Diazepam 1.25 mg/kg, P6 0.1 mg/kg | .2663 | |
| P1 0.1 mg/kg, P2 0.1 mg/kg | .4183 | |
| P1 0.1 mg/kg, P5 0.1 mg/kg | .5817 | |
| P1 0.1 mg/kg, P6 0.1 mg/kg | .0740 | |
| P2 0.1 mg/kg, P5 0.1 mg/kg | .1774 | |
| P2 0.1 mg/kg, P6 0.1 mg/kg | .0115 | S |
| P5 0.1 mg/kg, P6 0.1 mg/kg | .2080 | |

Parameter 7: $R_{tot}$ (No./5 min)

| | Animals | Mean | SD | SE |
|---|---|---|---|---|
| Vehicle CMC | 5.000 | 22.600 | 19.6800 | 8.801 |
| Diazepam 1.25 mg/kg | 8.000 | 68.750 | 31.4950 | 11.135 |
| P1 0.1 mg/kg | 8.000 | 60.375 | 23.8860 | 8.445 |
| P2 0.1 mg/kg | 8.000 | 60.250 | 28.7090 | 10.150 |
| P5 0.1 mg/kg | 8.000 | 69.500 | 20.3960 | 7.211 |
| P6 0.1 mg/kg | 8.000 | 75.625 | 11.6120 | 4.105 |

$R_{tot}$: ANOVA comparison

| | P-value | |
|---|---|---|
| Vehicle CMC, Diazepam 1.25 mg/kg | .0016 | S |
| Vehicle CMC, P1 0.1 mg/kg | .0083 | S |
| Vehicle CMC, P2 0.1 mg/kg | .0085 | S |
| Vehicle CMC, P5 0.1 mg/kg | .0013 | S |
| Vehicle CMC, P6 0.1 mg/kg | .0004 | S |
| Diazepam 1.25 mg/kg, P1 0.1 mg/kg | .4860 | |
| Diazepam 1.25 mg/kg, P2 0.1 mg/kg | .4795 | |
| Diazepam 1.25 mg/kg, P5 0.1 mg/kg | .9501 | |
| Diazepam 1.25 mg/kg, P6 0.1 mg/kg | .5669 | |
| P1 0.1 mg/kg, P2 0.1 mg/kg | .9917 | |
| P1 0.1 mg/kg, P5 0.1 mg/kg | .4480 | |
| P1 0.1 mg/kg, P6 0.1 mg/kg | .2078 | |
| P2 0.1 mg/kg, P5 0.1 mg/kg | .4419 | |
| P2 0.1 mg/kg, P6 0.1 mg/kg | .2042 | |
| P5 0.1 mg/kg, P6 0.1 mg/kg | .6098 | |

Parameter 8: $C_{tot}$ (No./5 min)

| | Animals | Mean | SD | SE |
|---|---|---|---|---|
| Vehicle CMC | 5.000 | 89.800 | 30.0870 | 13.455 |
| Diazepam 1.25 mg/kg | 8.000 | 144.375 | 60.4650 | 21.378 |
| P1 0.1 mg/kg | 8.000 | 137.000 | 25.7570 | 9.107 |
| P2 0.1 mg/kg | 8.000 | 108.375 | 27.7950 | 9.827 |
| P5 0.1 mg/kg | 8.000 | 127.500 | 20.3890 | 7.209 |
| P6 0.1 mg/kg | 8.000 | 153.750 | 32.9490 | 11.649 |

$C_{tot}$: ANOVA comparison

| | P-value | |
|---|---|---|
| Vehicle CMC, Diazepam 1.25 mg/kg | .0107 | S |
| Vehicle CMC, P1 0.1 mg/kg | .0258 | S |
| Vehicle CMC, P2 0.1 mg/kg | .3673 | |
| Vehicle CMC, P5 0.1 mg/kg | .0717 | |
| Vehicle CMC, P6 0.1 mg/kg | .0032 | S |
| Diazepam 1.25 mg/kg, P1 0.1 mg/kg | .6820 | |
| Diazepam 1.25 mg/kg, P2 0.1 mg/kg | .0508 | |
| Diazepam 1.25 mg/kg, P5 0.1 mg/kg | .3506 | |
| Diazepam 1.25 mg/kg, P6 0.1 mg/kg | .6027 | |
| P1 0.1 mg/kg, P2 0.1 mg/kg | .1171 | |
| P1 0.1 mg/kg, P5 0.1 mg/kg | .5979 | |
| P1 0.1 mg/kg, P6 0.1 mg/kg | .3542 | |
| P2 0.1 mg/kg, P5 0.1 mg/kg | .2909 | |
| P2 0.1 mg/kg, P6 0.1 mg/kg | .0152 | S |
| P5 0.1 mg/kg, P6 0.1 mg/kg | .1497 | |

Parameter 9: RW/TW (No./sec)

| | Animals | Mean | SD | SE |
|---|---|---|---|---|
| Vehicle CMC | 5.000 | .083 | .0810 | .036 |
| Diazepam 1.25 mg/kg | 8.000 | .124 | .0930 | .033 |
| P1 0.1 mg/kg | 8.000 | .155 | .1060 | .038 |
| P2 0.1 mg/kg | 8.000 | .099 | .0900 | .032 |
| P5 0.1 mg/kg | 8.000 | .123 | .0870 | .031 |
| P6 0.1 mg/kg | 8.000 | .190 | .0500 | .018 |

RW/TW: ANOVA comparison was not significant

| Parameter 10: CW/TW (No./sec) | | | | |
|---|---|---|---|---|
| | Animals | Mean | SD | SE |
| Vehicle CMC | 5.000 | .391 | .1150 | .052 |
| Diazepam 1.25 mg/kg | 8.000 | .599 | .2330 | .082 |
| P1 0.1 mg/kg | 8.000 | .454 | .1990 | .071 |
| P2 0.1 mg/kg | 8.000 | .420 | .1790 | .063 |
| P5 0.1 mg/kg | 8.000 | .448 | .0840 | .030 |
| P6 0.1 mg/kg | 8.000 | .515 | .1040 | .037 |

CW/TW: ANOVA comparison was not significant

The invention claimed is:

1. A compound of formula (II):

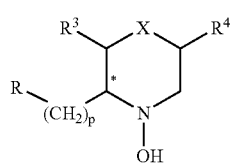

(II)

in which—

$R^3$ and $R^4$ each independently represent hydrogen or $C_{1-6}$ alkyl;

p represents 0 or 1; and

R represents a five- or six-membered saturated or unsaturated ring selected from:

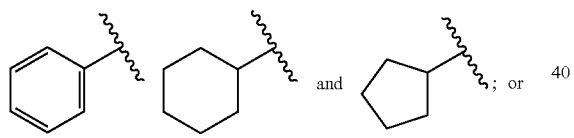

R represents a five- or six-membered substituted or unsubstituted unsaturated ring selected from:

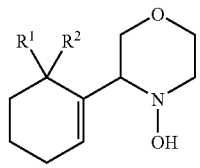

wherein $R^1$ and $R^2$ together represent an oxo group, or $R^1$ and $R^2$ each represent hydrogen, methoxy or ethoxy, or $R^1$ and $R^2$ together with the interjacent carbon atom represent a 1,3-dioxolane or 1,3-dioxane ring, attached via the 2 position and optionally bearing one or more methyl or ethyl groups;

or a tautomer thereof;

or a salt thereof.

2. A compound as claimed in claim 1 in which R represents a five- or six-membered substituted or unsubstituted unsaturated ring selected from:

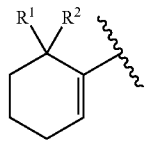 and 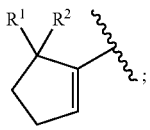

wherein $R^1$ and $R^2$ together represent an oxo group, or $R^1$ and $R^2$ each represent methoxy or ethoxy, or $R^1$ and $R^2$ together with the interjacent carbon atom represent a 1,3-dioxolane or 1,3-dioxane ring, attached via the 2 position and optionally bearing one or more methyl or ethyl groups, and p represents 0.

3. A compound as claimed in claim 1 in which $R^1$ and $R^2$ together represent an oxo group.

4. A compound as claimed in claim 1 in which R represents a five- or six-membered substituted or unsubstituted unsaturated ring selected from the group consisting of:

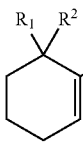 and 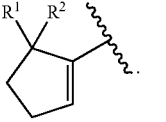

5. A compound as claimed in claim 1 in which $R^3$ and $R^4$ are identical.

6. A compound as claimed in claim 1 in which $R^3$ and $R^4$ each represents hydrogen.

7. A compound as claimed in claim 1 which is a compound of formula (III):

(III)

in which—

$R^1$ and $R^2$ each represent hydrogen or together represent an oxo group;

or a salt thereof.

8. A pharmaceutical composition comprising a compound of formula (II)

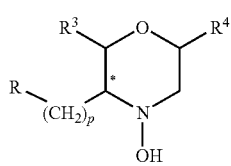

(II)

in which—

$R^3$ and $R^4$ each independently represent hydrogen or $C_{1-6}$ alkyl;

p represents 0 or 1; and

R represents a five- or six-membered saturated or unsaturated ring selected from:

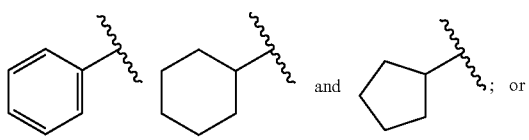 and ; or

R represents a five- or six-membered substituted or unsubstituted unsaturated ring selected from:

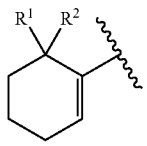 and 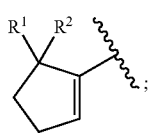 ;

wherein $R^1$ and $R^2$ together represent an oxo group, or $R^1$ and $R^2$ each represent hydrogen, methoxy or ethoxy, or $R^1$ and $R^2$ together with the interjacent carbon atom represent a 1,3-dioxolane or 1,3-dioxane ring, attached via the 2 position and optionally bearing one or more methyl or ethyl groups;

or a tautomer thereof;
or a salt thereof;
in association with a pharmaceutically acceptable carrier therefor.

9. A compound as claimed in claim 1 being of formula

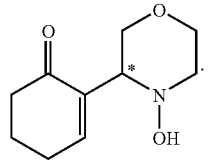

10. A pharmaceutical composition as claimed in claim 8 comprising a compound of formula

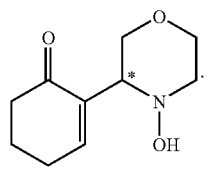

* * * * *

UNITED STATES PATENT AND TRADEMARK OFFICE
CERTIFICATE OF CORRECTION

PATENT NO.        : 7,842,689 B2                                Page 1 of 1
APPLICATION NO.   : 10/559180
DATED             : November 30, 2010
INVENTOR(S)       : Parsons et al.

It is certified that error appears in the above-identified patent and that said Letters Patent is hereby corrected as shown below:

Column 25, line 25, please delete the formula as follows:

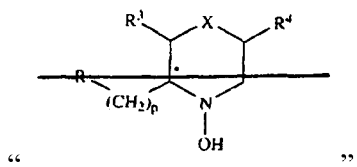

" "

and insert the formula as follows:

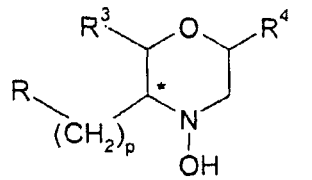

--                                                                        --

Signed and Sealed this
Nineteenth Day of April, 2011

David J. Kappos
*Director of the United States Patent and Trademark Office*